US009681860B2

(12) United States Patent
Steffen

(10) Patent No.: US 9,681,860 B2
(45) Date of Patent: Jun. 20, 2017

(54) HALO TIP SPRAY HEAD ATOMIZER DELIVERY MANIFOLD DEVICE

(71) Applicant: Dennis L Steffen, Tavernier, FL (US)

(72) Inventor: Dennis L Steffen, Tavernier, FL (US)

( * ) Notice: Subject to any disclaimer, the term of this patent is extended or adjusted under 35 U.S.C. 154(b) by 612 days.

(21) Appl. No.: 14/171,722

(22) Filed: Feb. 3, 2014

(65) Prior Publication Data
US 2015/0216516 A1 Aug. 6, 2015

(51) Int. Cl.
*A61B 17/00* (2006.01)

(52) U.S. Cl.
CPC ............ *A61B 17/00491* (2013.01); *A61B 2017/00495* (2013.01); *A61B 2017/00522* (2013.01); *A61B 2017/00544* (2013.01)

(58) Field of Classification Search
CPC ........... A61M 5/19; A61B 2017/00495; A61B 17/00491; A61B 2017/00522
See application file for complete search history.

(56) References Cited

U.S. PATENT DOCUMENTS

| 4,631,055 | A | 12/1986 | Redl |
| 5,368,563 | A | 11/1994 | Lonneman |
| 5,605,541 | A | 2/1997 | Holm |
| 6,394,982 | B1 | 5/2002 | Ehrenfels |
| 6,454,739 | B1 | 9/2002 | Chang |
| 6,458,095 | B1 | 10/2002 | Wirt |
| 6,461,325 | B1 | 10/2002 | Delmotte |
| 6,610,033 | B1 | 8/2003 | Melanson |
| 6,783,514 | B2 | 8/2004 | Tovey |
| 6,863,660 | B2 | 3/2005 | Marx |
| 7,037,289 | B2 | 5/2006 | Dodge |
| 7,883,501 | B2 | 2/2011 | McIntosh |
| 2009/0209916 | A1* | 8/2009 | Peindl ............... A61B 17/00491 604/173 |
| 2010/0065660 | A1* | 3/2010 | Hull ................. A61B 17/00491 239/428 |
| 2010/0168779 | A1* | 7/2010 | Redl ................. A61B 17/00491 606/185 |
| 2011/0319930 | A1* | 12/2011 | Roush ............... A61B 17/00491 606/213 |

FOREIGN PATENT DOCUMENTS

| WO | PCT/JP93/01364 | 1/1995 |
| WO | PCT/US97/03944 | 10/2002 |
| WO | PCT/US1996/019505 | 9/2004 |
| WO | PCT/US1999/009663 | 8/2005 |

* cited by examiner

Primary Examiner — Matthew F Desanto

(57) ABSTRACT

The present invention relates to a halo spray tip atomizer device primarily suited for the application of the fibrin glues. The device offers way to transition seamlessly between a static delivery device and an atomization device. The device is also so configured as to limit possible clogging.

12 Claims, 9 Drawing Sheets

SECTION 3-3

SECTION 2-2

SECTION 1-1

SECTION 3-3

HALO TIP SPRAY HEAD ATOMIZER DELIVERY MANIFOLD DEVICE

CROSS REFERENCES TO RELATED APPLICATIONS

This application claims the benefit under 35 U.S.C. §119 (e) of U.S. Non-Provisional application Ser. No. 12/258,076 filed on Oct. 24, 2008, and Provisional Application No. 61/887,359 filed on Oct. 5, 2013 the complete disclosure of which is incorporated herein by reference in its entirety.

FIELD OF THE INVENTION

The present invention relates to a Halo Tip Spray Head Atomizer Delivery Manifold Device.

INTRODUCTION

Conventional atomizers work by delivering a fine spray. Specialized devices are used for dispensing a plurality of different, i.e., separate, fluid medications or agents as an admixed product. For example, specialized spray heads are used for delivering two biochemically reactive fluids, such as fibrinogen and thrombin to form fibrin in an admixed state, to a biological surface. The biochemically reactive fluids may be delivered topically, in open-type surgeries such as laparotomic procedures, and in minimally invasive surgeries such as laparoscopic procedures.

There exist many techniques for the application of fibrin glues or sealants. In one method, the fibrin sealant components are drawn into a syringe and ejected via an appropriate sized needle. In another method, a double barrel syringe is used. Other conventional techniques include a microdrop delivery system, and a spray application via a multi-channel catheter, which is fixed, to a pressurized air/gas source. These conventional atomizers work by delivering the fibrin glue in a fixed non-adjustable spray pattern.

BRIEF DESCRIPTION

The Halo Tip Spray Head Atomizer Delivery Manifold Device in accordance with the present invention is especially useful with applications relating to the delivery of such admixtures as fibrin glues. It enables admixtures to be applied statically or through atomization to the specific site in a spray with use of the halo spray tip element or as a static delivery through its dual solution channels and deflectors.

The present invention relates to a halo spray tip atomizer delivery manifold; collectively comprised of a halo spray tip, solution channel insert, and delivery manifold. There exist many techniques for the application of fibrin glues. Application of the fibrin glue can be accomplished in a number of ways. Since fibrin glues exhibit a short set time (time it takes the admixture to harden) once the two biochemically reactive fluid solutions are combine it tends to have the issue of clogging the application device and clogging is always a concern and can be experienced in many of the current application methods. In one method, with admixture with a longer set time and not as prone to clogging the admixture is drawn into a single syringe and ejected via an appropriate sized needle. In another method a double barrel syringe is used and the two solutions are combined in some type of mixing chamber. Other conventional techniques employ a microdrop delivery system, a spray application via a multi-channel catheter which is fixed to a pressurized gas source. Additionally, a number of special applicators are commercially available. Although the example of the use of this invention focuses on fibrin glues it should not be construed as limited to only such application.

In one embodiment, the invention utilizes a halo spray tip atomizer delivery manifold which is connected to an air/gas source through the air channel of the manifold, thus utilizing the atomizer element of the invention. Additionally the air/gas exhaust apertures on the tip and apertures in the solution channel insert may also be varied in size and configuration to affect the particulate size being atomized.

In another embodiment, the invention utilizes a halo spray tip atomizer delivery manifold which is not connected to an air/gas source and not to the air channel of the manifold, thus utilizing only the solution channel insert apertures and solution deflectors on the tip to dispense and combine the two biochemically reactive fluid solutions to create an admixture.

In both afore mentioned, embodiments the fact that the two biochemically reactive fluid solutions are not combined until they are dispensed through the two solution channels and directed by the deflectors to converge into a single stream and finally combined. Depending on the admixture set time the device clogging issue is greatly reduced if not eliminated completely.

BRIEF DESCRIPTION OF THE DRAWINGS

The invention may be better understood and appreciated by reference to the detailed description of specific embodiments presented herein in conjunction with the accompanying drawings of which.

DETAILED DESCRIPTION

Figure 1:
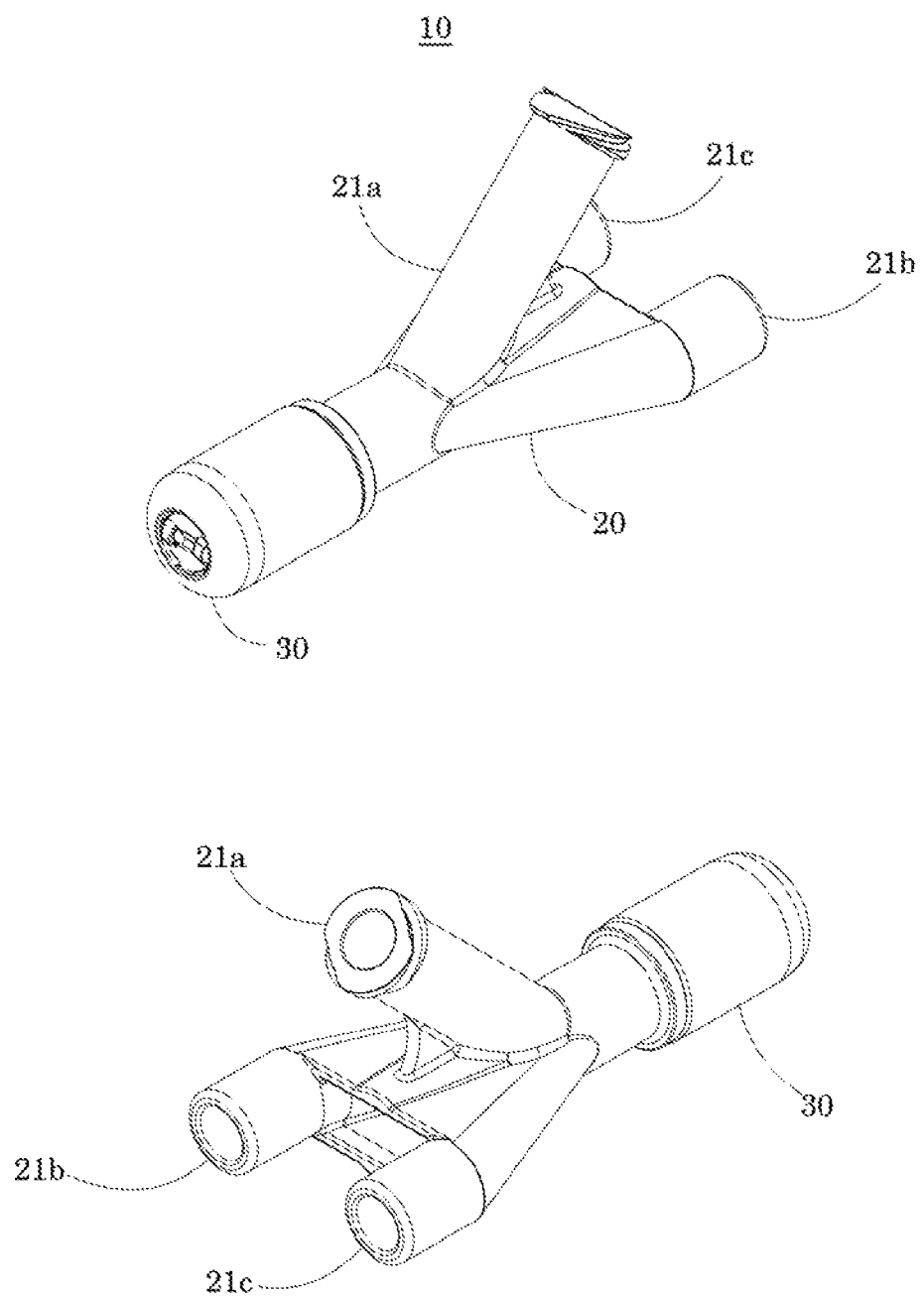
FIG. 1 is an isometric view of the distal and proximal perspective of the halo tip spray head atomizer delivery manifold device, all in accordance with the invention.
Figure 2:
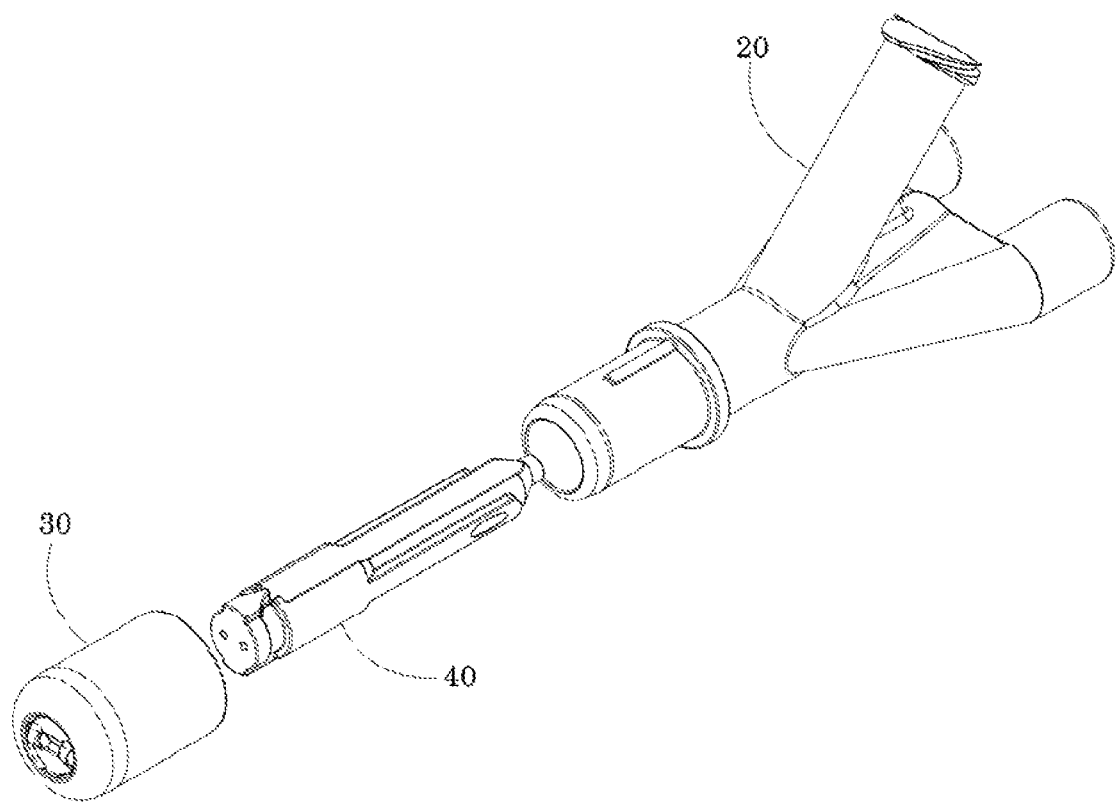
FIG. 2 is an isometric exploded view of the three components: halo tip, solution channel insert, and manifold of the halo tip spray head atomizer delivery manifold device, all in accordance with the invention.
Figure 3:
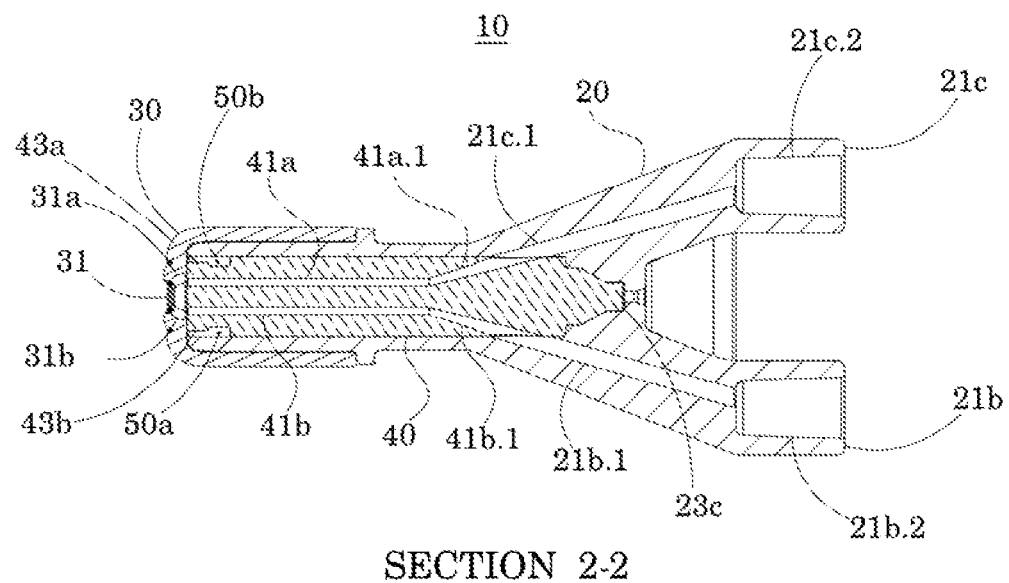
FIG. 3 is a side plan and cross section view of the, halo tip, solution channel insert and manifold components and their solution channels configuration of the halo tip spray head atomizer delivery manifold device, all in accordance with the invention.
Figure 3:
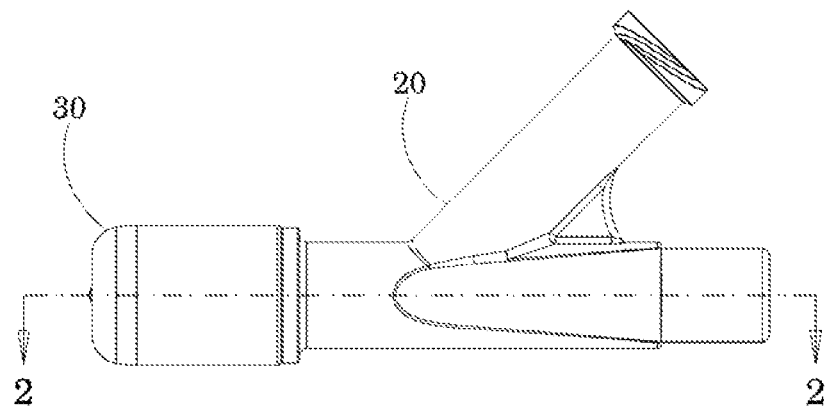

A fibrin glue delivery halo tip spray head atomizer delivery manifold device embodying the principles of the invention is provided. The device includes a manifold, a solution channel insert, and a specialized halo spray tip with a radial aperture exhaust configuration, solution stream deflectors, and capable of delivery of an admixture comprised of two biochemically reactive fluid solutions either statically or atomized.

Before any embodiments of the invention are explained in detail, it is to be understood that the invention is not limited in its application to the details of the structure and function set forth in the following description or illustrated in the appended drawings. The invention is capable of other embodiments and of being practiced or of being carried out in various ways. Also, it is to be understood that the phraseology and terminology used herein is for the purpose of description and should not be regarded as limiting. The use of "obround" herein is as defined per Merriam-Webster defines "obround" as having the form of a flattened cylinder with the sides parallel and the ends hemispherical. The use of "including," "comprising," or "having" and variations thereof herein is meant to encompass the items listed thereafter and equivalents thereof as well as additional items. "Comprising" also encompasses the terms "consisting of" and "consisting essentially of." The use of "consisting essentially of" means, e.g., that a method may include additional steps, but only if the additional steps do not materially alter the basic and novel characteristics of the claimed method. Unless specified or limited otherwise, the terms "joined", "mounted," "connected," "supported," and "coupled" and variations thereof herein are used broadly and encompass both direct and indirect mountings, connections, supports, and couplings. Further, "connected" and "coupled" are not restricted to physical or mechanical connections or couplings.

No admission is made that any reference, including any patent or patent document, cited in this specification constitutes prior art. In particular, it will be understood that unless otherwise stated, reference to any document herein does not constitute an admission that any of these documents forms part of the common general knowledge in the art in the United States or in any other country. Any discussion of the references states what the author asserts and the applicant reserves the right to challenge the accuracy and pertinence of any of the documents cited herein.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

Unless otherwise noted, technical terms are used according to conventional usage. However, as used herein, the following definitions may be useful in aiding the skilled practitioner in understanding the invention. Such definitions shall be applied, unless a different definition is given in the claims or elsewhere in this specification.

In view of the foregoing disadvantages inherent in conventional fibrin glue application systems, the invention provides a novel system and method for application of fibrin glues. The invention provides a dual function device for use as a non-air/gas assist static delivery device for the dispensing of fibrin glue without atomization as well as the air/gas assist halo spray tip element capable of dispensing the fibrin glue in the form of atomization onto a biological surface.

The full advantage of the combination of the static and halo tip atomization dispensing capabilities in accordance with the invention is realized when optimal spray area and particulate size are achieved through atomization, and additionally when atomization is not require then the static dispensing is utilized. Thus these two capabilities allows for the fibrin glue solution to be applied as effectively as possible while minimizing the device clogging issue communally associated with the application of fibrin glue.

Reference is now made to FIGS. 1-8 in which a halo tip spray head atomizer delivery manifold device, generally designated by reference numeral 10, in accordance with the invention is shown. Device 10 includes a manifold 20 and a halo spray tip 30 and solution channel insert 40 for delivery of fibrin glues comprised of two biochemically reactive fluid solutions. In an illustrated embodiment, manifold 20 is defined by non-converging unvalved first solution channel 21*b* and an unvalved second solution channel 21*c* which are opposed to the isolated unvalved third air/gas channel 21*a*. Manifold 20 connects to two solution sources e.g. syringes each syringe containing a single component of the two biochemically reactive fluid solutions and one air/gas source e.g. low pressure compressed air via the three luer connector fittings 21*c*.2, 21*b*.2 and 21*a*.3 which are configured to ISO 594-1 and -2 standard for 6% taper luer fittings. As presented in this specification the configuration of one female locking luer fitting for the unvalved air/gas channel 21*a* and two female slip luer fittings of the unvalved solution channels 21*b* and 21*c* of the manifold 20 can optionally be configured in varying combinations depending on requirements or as all female locking luer fittings or all female slip luer fittings (not illustrated in specification).

The manifold 20 includes a configuration FIG. 5 for the mating and orienting of the halo spray tip. The mating configuration on the manifold located in the distal area 22 joins with the inner aperture surface 33 of the halo tip 30 FIG. 6, the manifold distal area 22 also comprised of a proximal flange 22*a* and an orienting/anti-rotational protrusion element 22*b* which join with the recessed groove element 33*a* on the halo tip 30. When joined the combined elements prevent relative rotation between the two parts, facilitating orientation of the tip 30 to the manifold 20 and aligns the obround aperture 31 and deflectors 31*a* and 31*b* of the halo tip 30 with the unvalved apertures 41*a* and 41*b* of the solution channel insert 40. The manifold 20 distal area 22 has an aperture 22*c* which is proportioned to allow insertion and joining of the solution channel insert 40 with the manifold 20 a first rail channel 22*d* with an opposing second channel 22*e* located on the longitudinal center plane of manifold 20 that join with a first rail 42*a* and opposing second rail 42*b* of the solution channel insert 40. The air/gas channel of 21*a*1 of the manifold 20 has an outer surface 22*a*.1 which is proportioned to pass within the groove 44 of the solution channel insert 40.

As shown in FIG. 2, the solution channel insert 40 first joins with the manifold 20 and then secondly the halo spray tip 30 joins with the manifold 20 collectively comprising the device 10.

As shown in FIG. 3. A cross section 2-2 of the halo tip spray head atomizer delivery manifold device 10, illustrates the manifold 20 with its first 21*b* and second 21*c* unvalved solution channels with each channels having corresponding unvalved tapered channels 21*b*.1 and 21*c*.1 leading into the corresponding unvalved solution channels 41*a*.1 and 41*b*.1 which then leads into the corresponding unvalved channels 41*a* and 41*b* of the solution channel insert 40.

In a static method application the two biochemically reactive fluid solutions are introduced into the manifold 20 solution channels 21*b*.1 and 21*c*.1 via commonly actuable reservoirs then out though the corresponding solution channels 41*a*.1, 41*a*, and 41*b*.1, 41*b* in the solution channel insert 40 then through the exhaust aperture 31 in the halo spray tip 30 as individual fluid streams where they come in fluid contact with the concave surfaces of the solution deflectors 31a and 31b of the exhaust aperture 31 in the halo spray tip 30. The solution deflectors 31a and 31b facilitate the joining/directing resulting in convergence of the two solution fluid streams as they exit the exhaust aperture 31 which results in the creation of the admixture.

In a atomization method application as in the use of pressured air/gas the introduction of the two biochemically reactive fluid solutions are as afore described wherein the two solution streams exiting through the exhaust aperture 31 are joined/directed by the deflectors 31a and 31b to converge and create the admixture which is then picked up by the air/gas exhaust which has entered through the isolated unvalved air channel 21a.2 and then through 21a.1 of the manifold 20 the air/gas is then diverter by the air/gas diverter 46 of the solution channel insert 40 and exhausted over surfaces 43a and 43b lastly through the apertures 32a, 32b, 32c, and 32d and in direct contact with the concave inner surfaces 3.2a.1, 32b.1, 32c.1, and 32d.1 of the halo spray tip 30 which results in an atomization of the admixture in a halo effect. The pressure equalizing plenum chambers 50a and 50b created when the solution channel insert 40 and manifold 20 are joined acts to equalize and distribute the air/gas equally through the exhaust apertures 32a, 32b, 32c, and 32d of halo spray tip 30.

Figure 4:
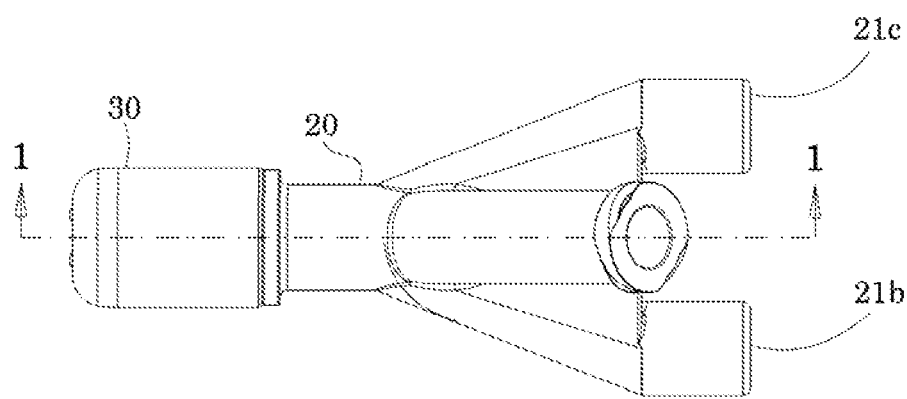
FIG. 4 is a top plan and cross section view of the, halo tip, solution channel insert and manifold components and their air/gas channels configuration of the halo tip spray head atomizer delivery manifold device, all in accordance with the invention.
Figure 4:
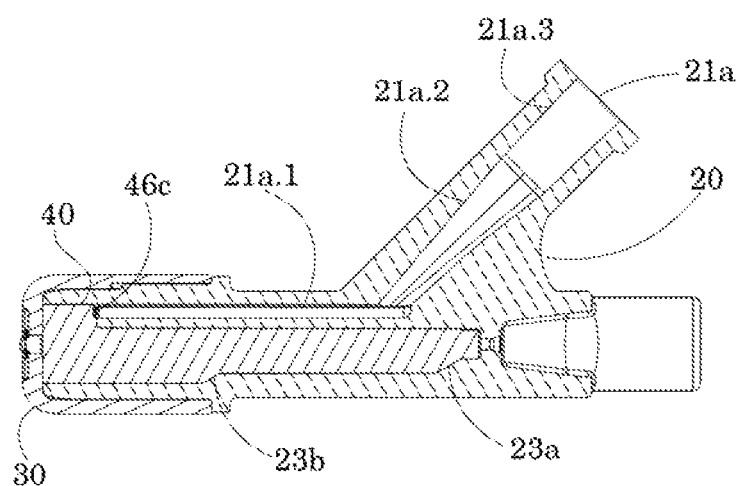

As shown in FIG. 4, cross section 1-1 of the halo tip spray head atomizer delivery manifold device 10, the manifold 20 has an isolated air/gas channel 21a leading into 21a.2 then 21a.1 which traverses along the groove 44 of the solution channel insert 40 and then terminating at the proximal tip 46c of the air/gas deflector 46 of the solution channel insert 40. As air/gas pressure is applied during an atomization application the air/gas is deflected to either side 46a and 46b of the deflector 46 of the solution channel insert 40 and into the recessed area 45a and 45b which act to create the pressure equalizing plenum chambers 50a and 50b when joined with the manifold 20 as previously described. The equally pressurized air/gas then exhaust through the apertures 32a, 32b, 32c, and 32d, these apertures, FIG. 7, cross section 3-3 have concave inner surfaces 32a.1, 32b.1, 32c.1, and 32d.1 (32b.1 and 32d.1 not shown in specification) the concave of the aperture inner surface acts to defect the air/gas as it is exhausted resulting in a halo effect.

Figure 5:
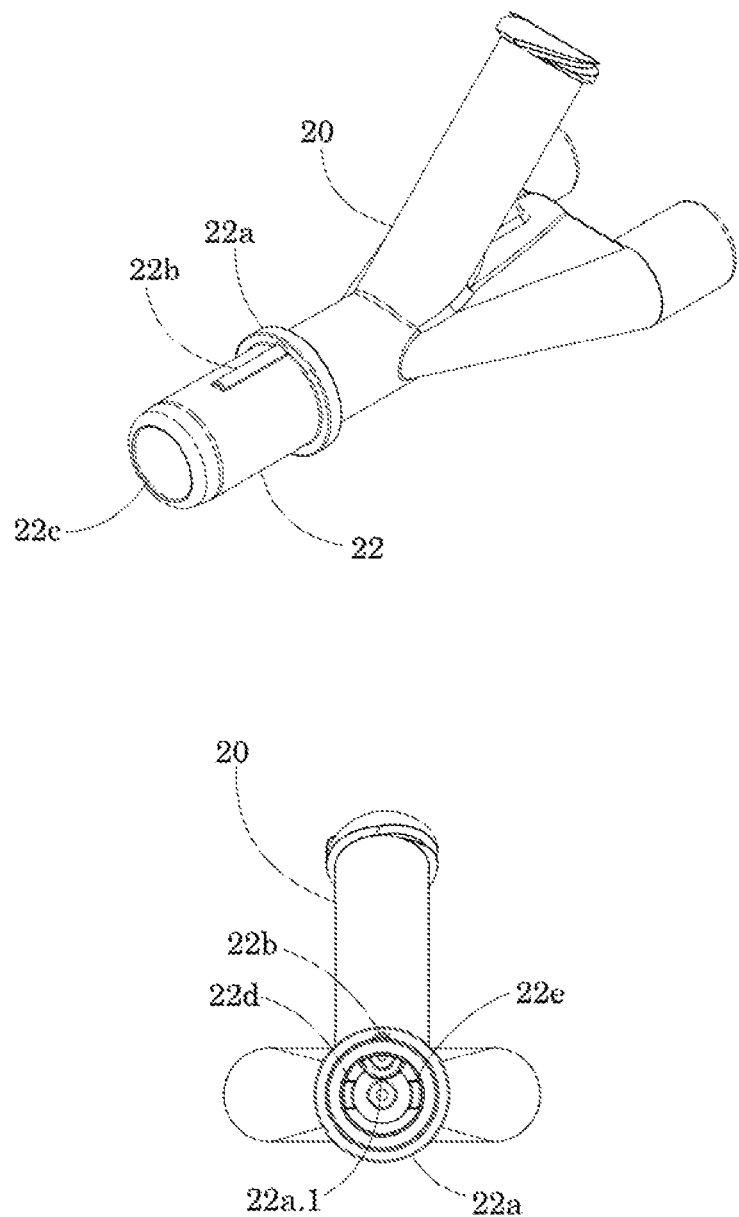
FIG. 5 is a front plan and isometric view of the atomizer manifold with the halo tip and solution channels insert removed, all in accordance with the invention.

As shown in FIG. 5, further illustrates the distal portion 22 of the manifold 20 which corresponds with a matting orifice 33 of the halo spray tip 30, a raised protrusion 22b of the distal portion 22 corresponds with the groove 33a of the halo spray tip 30 providing positioning of the exhaust aperture 31 in relationship to the solution channels apertures 41a and 41b of the solution channel insert 40 when the manifold 20, solution channel insert 40 and halo spray tip 30 are joined together as shown in FIG. 1.

Figure 6:
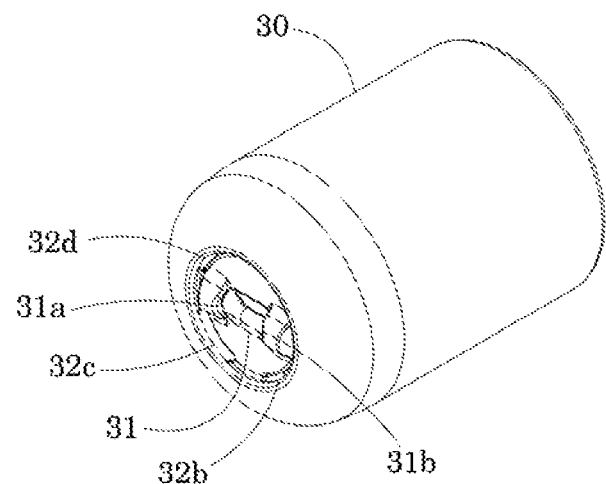
FIG. 6 is an isometric view of the distal and proximal perspective of the halo tip, all in accordance with the invention.
Figure 6:
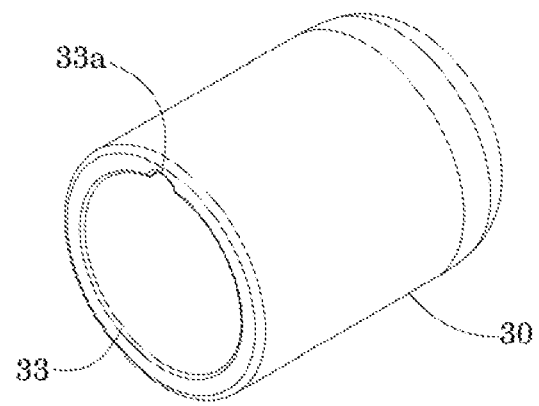
Figure 7:
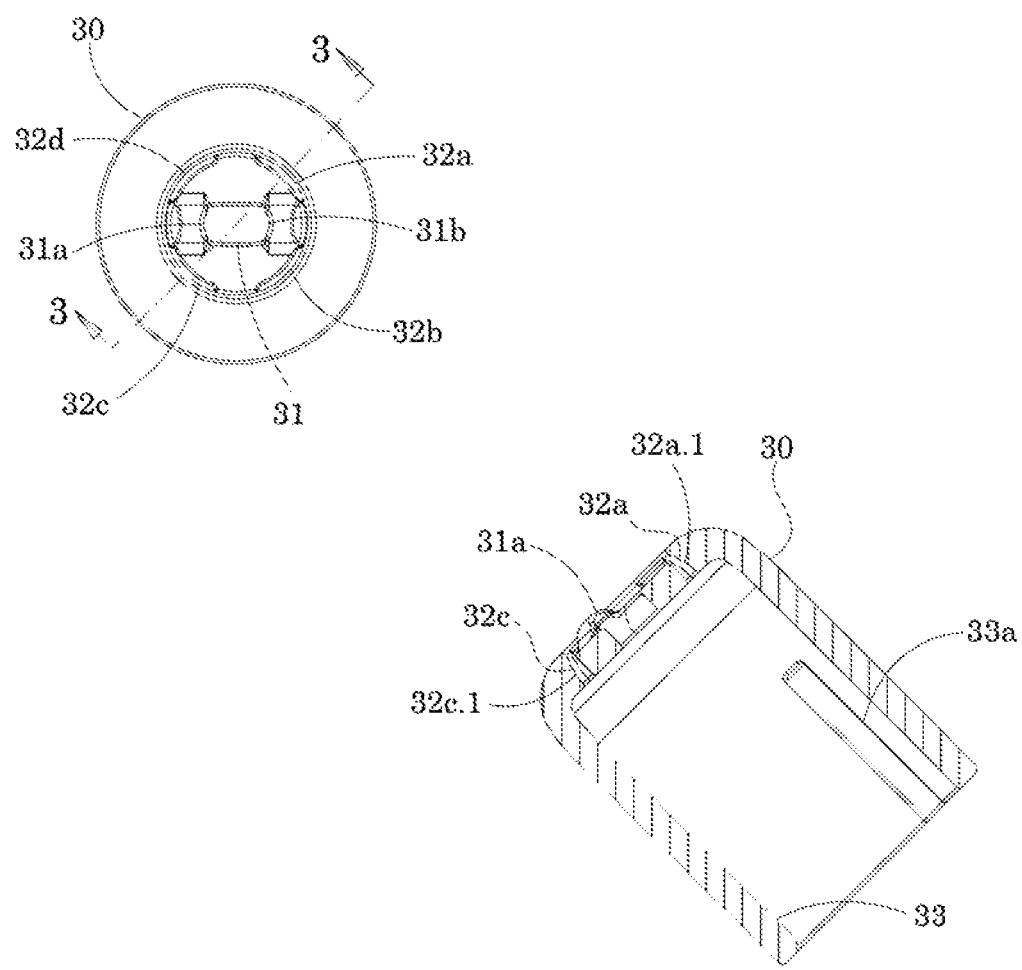
FIG. 7 is a front plan view and cross section view of the halo tip, all in accordance with the invention.

As shown in FIG. 6 isometric views of the distal and proximal perspective and FIG. 7 front plan and cross section view 3-3 of the halo spray tip embodiment is further illustrated with the radially positioned air/gas exhaust apertures 32a, 32b, 32c, 32d and their inner concave surfaces 32a.1 and 32c.1 illustrated in cross section 3-3 along with the solution exhaust aperture 31 and solution stream deflectors 31a and 31b all lying about the longitudinal centerline; corresponding concave surfaces 32b.1 and 32d.1 relating to apertures 32b and 32d not shown in illustrations.

Figure 8:
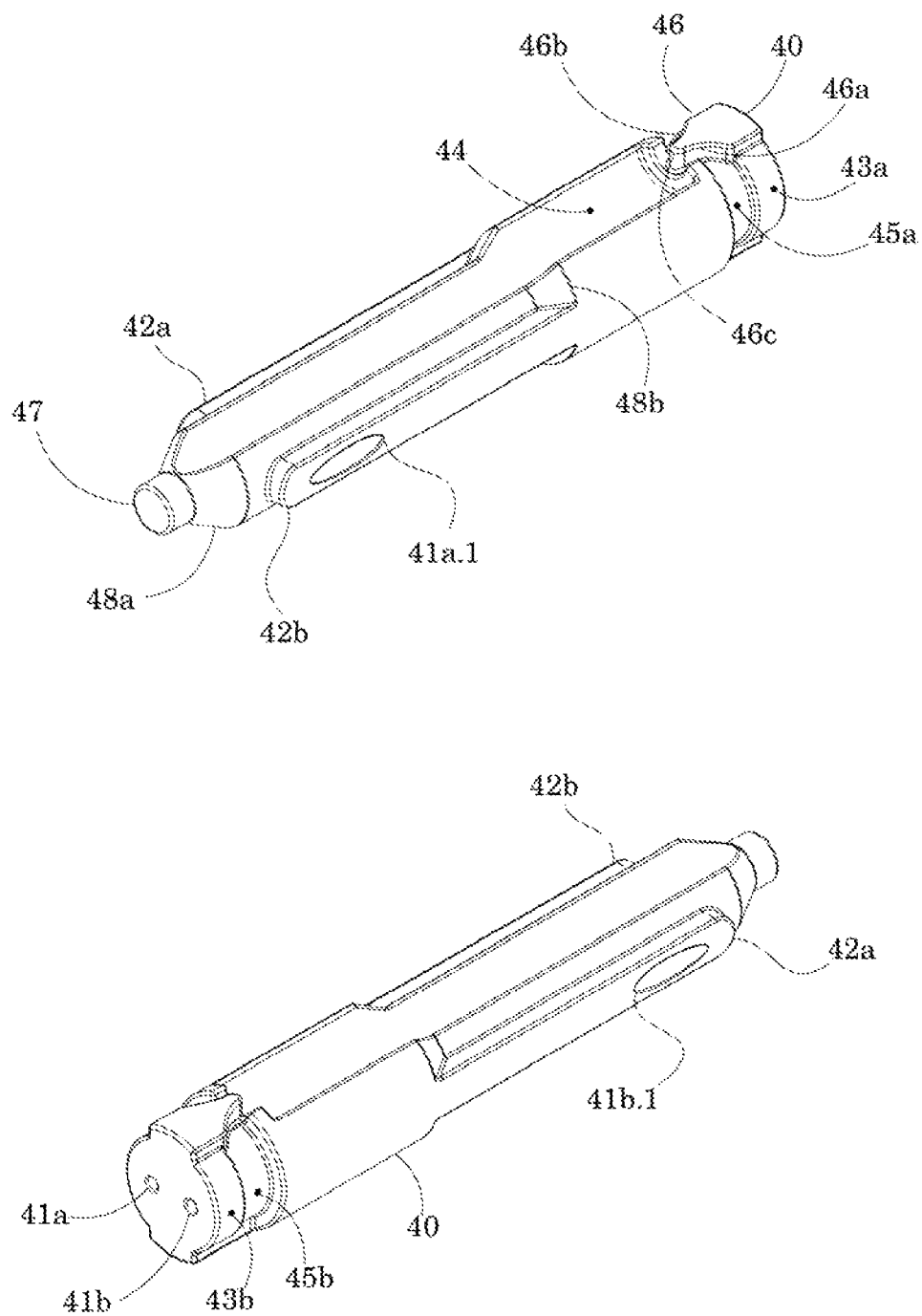
FIG. 8 is an isometric view of the distal and proximal perspective of the solution channel insert, all in accordance with the invention.

As shown in FIG. 8 isometric views of the distal and proximal perspective of the solution channel insert, is further illustrated with the two solution channels 41a and 41b, with their corresponding inlet apertures 41a.1, and 41b.1 that interface with the solution channels of the manifold 21b.1 and 21c1. Additionally illustrated are the two rails 42a and 42b which correspond with the rail channels 22d and 22e of the manifold 20. Also further illustrated is the groove 44 which corresponds to the isolated air/gas channel outer surface 22a.1. Although the presented embodiment illustrates the air/gas channel portion 21a.1 as sell-contained and joined to the manifold 20 it may also be configured and combined as part of the solution channel insert. The two recessed surfaces of the solution channel insert 40 with a first surface 43a and second surface 43b define the air/gas exhaust zones/apertures created between the inner surfaces of the distal aperture 22c of the manifold 20 the two apertures align with the radial apertures 32a, 32b, 32c, and 32d of the tip 30. Two angled surfaces 48a and 48b correspond to surfaces 23a and 23b of the manifold 20 to create a positive seal when the components are joined. The solution channel insert 40 has a proximal protrusion 47 which corresponds with a recess 23c of the manifold 20 which ensures proper positioning/alignment of the solution channel insert 40.

Figure 9:
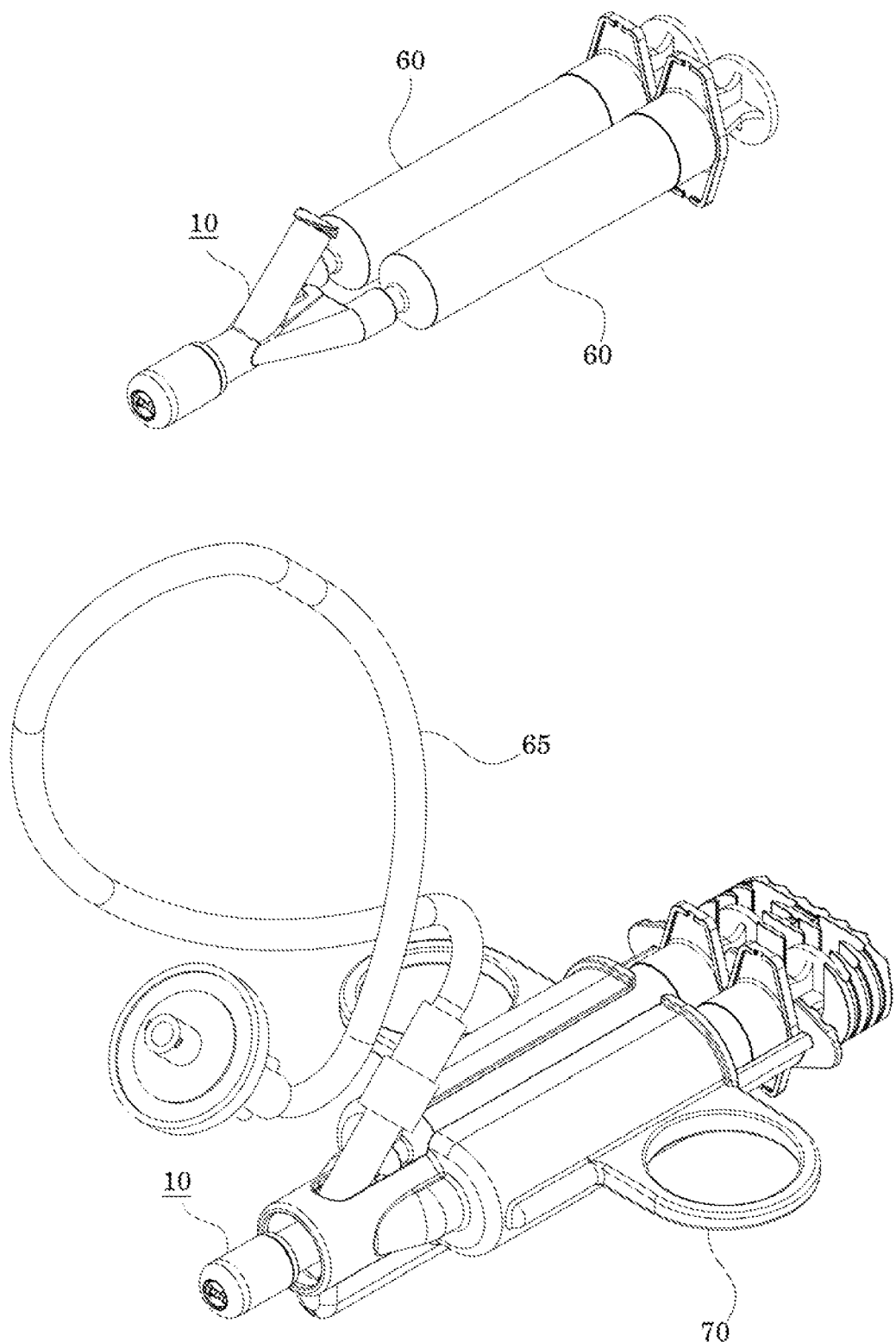
FIG. 9 is an isometric view of the halo tip spray head atomizer delivery manifold device as combined in stages first with the solution source e.g. syringes then with a delivery system and air/gas source, all in accordance with the invention.

As shown in FIG. 9 an isometric view of the embodiment is illustrated with the two stages of how the halo tip spray head atomizer device 10 would be applied first the device 10 is connected with the two solution source syringes 60 and then placed into a delivery system 70 and connected to an air/gas source 65 for application to a biological surface.

In practice, the invention provides a method of dispensing fibrin glues to a biological surface. The method includes a halo tip spray head atomizer delivery manifold device capable of a static delivery method or accepting standard air/gas sources for an atomization method and with both methods capable of accepting solution delivery systems e.g. syringes or commonly actuable reservoirs.

The foregoing description is considered as illustrative only of the principles of the invention. Further, since numerous modifications and changes may readily occur to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. Alt publications, patents and patent applications are herein expressly incorporated by reference to the same extent as if each individual publication or patent application was specifically and individually indicated by reference, in case of conflict between the present disclosure and the incorporated patents, publications and references, the present disclosure should control.

The invention claimed is:

1. An atomizer delivery device with capability of static or atomized solution deployment comprising:
   a manifold with first solution channel,
      a second solution channel,
      a gas channel;
   a solution channel insert with isolated gas channel and two parallel solution channels matingly joined and aligned with said manifold gas, and first and second channels; and
   a halo spray tip having an outer distal surface with a central aperture and set of external deflectors;

wherein said atomizer delivery device is configured to allow fluids to be deployed through said manifold solution channels then traversing through said corresponding solution channels in said solution channel insert then exhausted through said central aperture in said halo spray tip as individual fluid streams where they come in fluid contact with said external deflectors of said halo spray tip resulting in convergence of the two fluid streams which results in the creation of an admixture, wherein said halo spray tip is configured to deflect said admixture through multi apertures resulting in a halo spray effect.

2. The atomizer delivery device of claim 1, wherein said halo spray tip comprises said multi apertures lying in a radial position to a longitudinal centerline comprised of concave inner surfaces of said multi apertures, wherein air/gas combines with said admixture resulting in said halo spray effect.

3. The atomizer delivery device of claim 2, wherein said solution channel insert comprises an air/gas flow diverter, wherein air/gas flow is diverted equally through said halo spray tip multi apertures.

4. The atomizer delivery device of claim 1, wherein said halo spray tip has a recessed groove element configured to matingly join to a protrusion element on said manifold, said recessed groove element and said protrusion element are configured to insure alignment of said central aperture and said external deflectors of said halo spray tip to said solution channels of said solution channel insert.

5. The atomizer delivery device of claim 1, wherein said halo spray tip further includes said central aperture bounded by said set of said deflectors on said halo spray tip outer distal surface.

6. The atomizer delivery device of claim 1, wherein said halo spray tip comprises said multi apertures lying in a radial position to a longitudinal centerline.

7. The atomizer delivery device of claim 1, wherein said first solution channel and second solution channel of the solution channel insert are unvalved.

8. The atomizer delivery device of claim 1, wherein the solution channel insert comprises a multi air/gas pressure equalizing plenum chambers.

9. The atomizer delivery device of claim 1, wherein the solution channel insert comprises multi air/gas exhaust zones.

10. The atomizer delivery device of claim 1, wherein a first solution channel inlet and a second solution channel inlet are configured to accept a 6% taper female locking luer fitting and a gas channel inlet is configured to accept a 6% taper female locking luer fitting.

11. The atomizer delivery device of claim 1, wherein said first solution channel inlet and said second solution channel inlet are configured to accept a 6% taper female slip luer fitting and said gas channel inlet is configured to accept a 6% taper female slip luer fitting.

12. A spray atomizer system for delivering two biochemically reactive fluid mixtures in a halo spray pattern, comprising:

a manifold first joined with a solution channel insert then secondly a halo spray tip joins with the manifold, said manifold having solution conduits and a gas conduit, and said solution channel insert having parallel conduits for receiving two biochemically reactive fluids and said solution channel insert having a gas channel for receiving gas or air, and said halo spray tip having a distal aperture bounded by a set of external deflectors on a distal surface and further included a plurality of apertures in a radial pattern, wherein said halo spray tip being configured to be in direct mating relationship and in fluid communication with a distal end of said manifold, said manifold having a protrusion on an exterior surface configured to join with a recess on an interior surface of said halo spray tip, said protrusion and said recess are configured to align said distal aperture of said halo spray tip, wherein said halo spray tip distal aperture allows said fluids to be dispensed and come into fluid contact with said external deflectors so that said fluids are directed by inner surfaces of said halo spray tip external deflectors and form an admixture, and wherein said radial apertures are configured to atomize said admixture in a halo effect.

* * * * *